US005763552A

United States Patent [19]

Feiring et al.

[11] Patent Number: 5,763,552

[45] Date of Patent: Jun. 9, 1998

[54] HYDROGEN-CONTAINING FLOUROSURFACANT AND ITS USE IN POLYMERIZATION

[75] Inventors: Andrew E. Feiring; Ming-Hong Hung, both of Wilmington; Jose M. Rodriguez-Parada, Hockessin, all of Del.; Roger J. Zipfel, Washington, W. Va.

[73] Assignee: E. I. du Pont de Nemours and Company, Wilmington, Del.

[21] Appl. No.: 886,389

[22] Filed: Jul. 1, 1997

Related U.S. Application Data

[60] Provisional application No. 60/022,817 Jul. 26, 1996.

[51] Int. Cl.$^6$ .............................. C08F 2/00; C07C 69/63

[52] U.S. Cl. .......................... 526/214; 560/184; 560/227; 562/586; 562/605; 568/842; 570/137

[58] Field of Search .................................... 560/184, 227; 562/586, 605; 568/842; 570/137; 526/214

[56] References Cited

U.S. PATENT DOCUMENTS 2,856,439 10/1958 Helmut .
3,819,594 6/1974 Holmes et al. .................... 260/87.5 A
4,360,618 11/1982 Trementozzi .......................... 524/141
4,380,618 4/1983 Khan et al. .
4,381,384 4/1983 Khan .
4,384,092 5/1983 Blaise et al. .
4,720,578 1/1988 Lin .
4,725,375 2/1988 Fujii et al. .

FOREIGN PATENT DOCUMENTS 1067068 5/1967 United Kingdom .

OTHER PUBLICATIONS

In-house computer abstract pp. 17–19; Answer 11 of 17 Ohsaka et al. JP 83-251 069 -83 1226.

*Primary Examiner*—Joseph L. Schofer
*Assistant Examiner*—N. Sarofim

[57] ABSTRACT

A partially-fluorinated surfactant having internal methylene groups and having the formula $R_f$—$(CH_2)_m$—$R'_f$—COOM wherein m is 1–3, $R_f$ is perfluoroalkyl or perfluoroalkoxy, containing 3–8 carbon atoms, $R'_f$ is linear or branched perfluoroalkylene containing 1–4 carbon atoms, and M is $NH_4$, Li, Na, K, or H is useful in polymerization of fluorinated monomers. High molecular weight can be achieved in homopolymerization of tetrafluoroethylene.

13 Claims, No Drawings

HYDROGEN-CONTAINING FLOUROSURFACANT AND ITS USE IN POLYMERIZATION

This application claims the benefit of provisional application Ser. No. 60/022.817 filed July 26, 1996.

FIELD OF THE INVENTION

This invention is in the field of fluorinated compounds useful as surfactants in processes for polymerizing fluorinated monomers.

BACKGROUND OF THE INVENTION

The industry standard for the aqueous dispersion polymerization of perfluorinated monomers has been the use of perfluoroalkanoate dispersing agents, and in particular those containing an average of 8 carbon atoms. This dispersing agent, usually ammonium perfluorooctanoate which is frequently called C-8, is disclosed in countless publications describing the polymerization of tetrafluoroethylene (TFE) by itself or with other monomers.

Fluorinated surfactancts that are not perfluorinated have been used as dispersing agents in the aqueous dispersion polymerization of TFE by itself or in combination with other copolymerizable fluorinated ethylenically unsaturated comomomers. U.S. Pat. No. 4,380,618 discloses, for example, the use of certain perfluoroalkyl ethane sulfonic acids and salts thereof having the general formula $F(CF_2)_n—CH_2—CH_2—SO_3M$ in TFE polymerizations. TFE homopolymer made in Examples 4 and 5 of this patent exhibited standard specific gravity (SSG) values of 2.215 and 2.218, respectively. SSG is an indirect indicator of molecular weight, a parameter that increases with decreasing molecular weight. The SSG values of the '618 patent do not reflect very high molecular weight, because of chain transfer attributable to the hydrogens in the surfactant.

SUMMARY OF THE INVENTION

This invention provides a partially-fluorinated surfactant that is useful in the polymerization of fluorinated monomers and which, despite the presence of hydrogen, permits the attainment of high molecular weight when used in homopolymerization of tetrafluoroethylene.

Specifically, the invention provides a compound having the formula $R_f—(CH_2)_m—R'_f—COOY$, wherein m is 1–3, $R_f$ is perfluoroalkyl or perfluoroalkoxy containing 3–8 carbon atoms, $R'_f$ is linear or branched perfluoroalkylene containing 1–4 carbon atoms, Y is M or R, M is $NH_4$, Li, Na, K or H, and R is linear, branched or cyclic alkyl containing 1–8 carbon atoms. The invention further provides additional compounds useful as intermediates in the preparation of the above compound.

In a further embodiment of the invention, a process for polymerization of fluorinated monomers using the partially-fluorinated surfactant of the invention is provided.

DETAILED DESCRIPTION

It has been discovered that a new family of hydrogen-containing surfactants can be used in polymerization of fluorinated monomers. Surprisingly, despite the presence of hydrogen, chain transfer during polymerization is very low as shown by examples below.

The surfactants of this invention have the general formula $$R_f—(CH_2)_m—R'_f—COOM \tag{I}$$

wherein m is 1–3, $R_f$ is perfluoroalkyl or perfluoroalkoxy, preferably perfluoroalkyl, containing 3–8 carbon atoms, $R'_f$ is linear or branched perfluoroalkylene containing 1–4 carbon atoms, and M is $NH_4$, Li, Na, K, or H. $R_f$ can be branched, for example, by terminating with $—(CF_3)_2$. Preferably, m is 1–2, $R_f$ is linear perfluoroalkyl having 4–6 carbon atoms, $R'_f$ is linear perfluoroalkylene having 1–2 carbon atoms and M is $NH_4$ or H. For use in polymerization of fluorinated monomers, $M{=}NH_4$ is especially preferred.

Surfactants (I) can be prepared by reduction of iodine-containing intermediate esters having the general formula $$R_f—(CH_2)_x—CHI—(CH_2)_y—R'_fCOOR \tag{II}$$

wherein x and y are independently 0 or 1, $R_f$ and $R'_f$ are as defined above, and R is linear, branched or cyclic alkyl containing 1–8 carbon atoms, to form esters having the formula $$R_f—(CH_2)_m—R'_fCOOR \tag{III}$$

followed by acid hydrolysis to form the acid (M=H), and reaction with base to form the salts (M=Li, Na, K, $NH_4$). The iodine-containing esters (II) are an aspect of the invention. Preferably, x+y=1 in order to obtain m=2. The reduction of iodine-containing intermediates (II) to form (III) can be carried out, for example, by catalytic hydrogenation or by reaction with tributyltin hydride.

The iodine-containing intermediates (II) can be prepared by reacting fluoroalkyl or fluoroalkoxy ethylene having the formula $$R_f—(CH_2)_x—CH{=}CX_2 \tag{IV}$$

wherein X is H or F, and $R_f$ and x are as defined above, with iodinated ester having the general formula $$I—R'_f—COOR \tag{V}$$

wherein R'fand R are as defined above. The reaction of substituted ethylene (IV) with iodinated ester (V) to form the iodine-containing ester (II) can be carried out at elevated temperature in the presence of copper, and the product iodine-containing ester (II) can be isolated by standard procedures.

Iodinated esters (V) can be made by the reaction of iodine monochloride, chlorosulfonic or fluorosulfonic acid, and a perfluorinated olefin chosen to yield the desired $R'_f$, followed by alcohol quench.

The esters (II) and (III) are aspects of the present invention. Preferably, x+y is 0 or1, $R_f$ is linear perfluoroalkyl having 4–6 carbon atoms, $R'_f$ is linear perfluoroalkylene having 1–2 carbon atoms, and R is methyl or ethyl.

The process comprising reacting iodinated ester (V) with substituted ethylene (IV) to obtain the iodinated ester (II), followed by reduction to obtain the ester (III), followed by acid hydrolysis to obtain compound (I) with M=H is an aspect of the present invention. The process further comprising reaction with base to obtain (I) wherein M is $NH_4$, Li, Na or K is an additional aspect of the invention.

When m=1, surfactants (I) can be prepared by reaction of perfluoroalkyl or perfluoroalkoxy iodide $R_fI$ with vinylidene fluoride to form one-to-one and one-to-two iodinated adducts, $R_f—CH_2CF_2I$ and $Rf—CH_2CF_2—CH_2CF_2I$, respectively. The one-to-one adduct is reacted with LiCl to form the terminal vinyl —CH=$CF_2$, followed by reaction with methanol in the presence of a radical initiator to form Rf—$CH_2CF_2$—$CH_2OH$, followed by oxidation to convert the —$CH_2OH$ to —COOH. The one-to-two adduct may also be treated with LiCl to form the terminal vinyl compound, followed by oxidation to convert the vinyl to —COOH. Alternatively, the one-to-one iodinated adduct can be reacted with an appropriate perfluoroolefin to form an iodinated adduct which is oxidized to —COOH. In these sequences, the acid can be reacted with base to form the $NH_4$, Li, Na or K salt. Compounds obtained by these steps have the formula $$R_f—CH_2—R'_f—A \quad (VI)$$

wherein $R_f$ is perfluoroalkyl or perfluoroalkoxy containing 3–8 carbon atoms, $R'_f$ is linear or branched perfluoroalkylene containing 1–4 carbon atoms, A is $CF_2I$, $CH_2OH$, COOM or COOR, M is $NH_4$, Li, Na, K, or H, and R is linear, branched or cyclic allyl containing 1–8 carbon atoms. Such compounds are an aspect of this invention. Preferably, $R_f$ is linear perfluoroalkyl having 4–6 carbon atoms, $R'_f$ is linear perfluoroalkylene having 1–2 carbon atoms, M is $NH_4$ or H, and R is methyl or ethyl.

The process comprising reacting $R_f$—$CH_2CF_2I$ with alkali metal salt such as LiCl to form the terminal vinyl $R_f$—CH=$CF_2$, followed by reaction with alcohol such as methanol in the presence of a radical initiator to form (VI) with $R'_f$=CF2 and A =$CH_2OH$, followed by oxidation to form (VI) with A=COOH is an aspect of the present invention. The process further comprising reaction with base to obtain (VI) with A=COOM wherein M is $NH_4$, Li, Na or K is an additional aspect of the invention.

The aqueous dispersion polymerization process of the present invention is conventional except for the use of $R_f$—$(CH_2)_m$—$R'_f$—COOM (I) as the dispersing agent for the polymerization of fluorinated monomer. Organic liquid such as 1,1,2-trichloro-1,2,2-trifluoroethane can be present in the aqueous medium, but solvent-free aqueous dispersion polymerization is preferred. The initiator is water-soluble, and will generally be used in the amount of 2–500 ppm based on the weight of water present. Examples include ammonium persulfate, potassium persulfate, potassium permanganate, and disuccinic acid peroxide. The polymerization can be carried out by charging the polymerization reactor with water, surfactant, monomer, and optionally chain transfer agent, agitating the contents of the reactor, and heating the reactor to the desired polymerization temperature, e. g. 50°–110° C., and then adding initiator at the desired rate to start and continue the polymerization. Additional monomer can be added to the reactor to replenish monomer that is consumed.

Fluorinated monomers, i.e., monomers containing at least 35 wt % fluorine, that can be polymerized in the process of this invention include fluoroolefins having 2–10 carbon atoms, fluorinated dioxoles, and fluorinated vinyl ethers of the formula $CY_2$=CYOR or $CY_2$=CYOR'OR wherein Y is H or F, and —R, and —R'— are independently completely-fluorinated or partially-fluorinated alkyl and alkylene groups containing 1–8 carbon atoms. Preferred —R groups contain 1–4 carbon atoms and are preferably perfluorinated. Preferred —R'— groups contain 2–4 carbon atoms and are preferably perfluorinated. Preferred fluoroolefins have 2–6 carbon atoms and include TFE, hexafluoropropylene (HFP), chlorotrifluoroethylene (CTFE), vinyl fluoride, vinylidene fluoride, trifluoroethylene, hexafluoroisobutylene, and perfluorobutyl ethylene. Preferred cyclic fluorinated monomers include perfluoro-2,2-dimethyl-1,3-dioxole (PDD) and perfluoro-2-methylene-4-methyl-1,3-dioxolane (PMD). Preferred fluoropolymers include the group of tetrafluoroethylene (TFE) polymers. Preferred TFE polymers include perfluoropolymers, particularly TFE homopolymers and copolymers of TFE and one or more of perfluoroolefins having 3–8 carbon atoms, especially HFP, and perfluoro (alkyl vinyl ethers) having alkyl groups containing 1–5 carbon atoms, especially 1–3 carbon atoms.

Fluoropolymers made by the process of this invention can be glassy, plastic, or elastomeric. They can be amorphous or partially crystalline, melt-fabricable or non-melt-fabricable.

When tetrafluoroethylene (TFE) is polymerized according to the process of this invention, pressure is typically in the range of 0.3 to 7 MPa and TFE is usually pressured into the reactor at a rate to maintain pressure at a target value. TFE may be the only monomer used, in which case the polytetrafluoroethylene (PTFE) formed will be homopolymer. Alternatively, an amount of copolymerizable perfluorinated comonomer other than TFE can be added to the reactor to copolymerize with the TFE wherein the resultant TFE polymer is modified with less than 0.5 mol % of the comonomer to impart at least improved film forming properties upon sintering, while still retaining the PTFE character of the polymer (modified PTFE). The PTFE will generally be non-melt-fabricable, i.e., it will have a melt viscosity exceeding $1\times10^9$ Pa.s at 380° C. Melt viscosity in this range is measured at 380° C. by the tensile creep method in U.S. Pat. No. 3,819,594. Chain transfer agent, such as ethane or methanol, can be present during the polymerization reaction to provide lower melt viscosity PTFE, e.g., 10 Pa.s to 1 ×105 Pa.s measured at 372° C. Comonomer, if present, will preferably be perfluoro(alkyl vinyl ether), wherein the alkyl group contains 1 to 8 carbon atoms, preferably 2 or 3 carbon atoms, perhaloolefin such as chlorotrifluoroethylene, perfluoroolefin such as hexafluoropropylene, or perfluoroalkyl olefin such as perfluorobutyl ethylene. More than one modifying comonomer can be used. The polymerization is carried out to achieve the desired polymer solids concentration in the aqueous dispersion, e.g. 20 to 60% based on the combined weight of water and polymer solids, and the polymerization is stopped by stopping the TFE feed and venting the reactor to remove unreacted monomer, optionally allowing the reaction to continue for some time after stopping TFE feed and before venting.

When the polymerization process of this invention is used to make a melt-fabricable TFE copolymer, the amount of comonomer added will be effective to incorporate sufficient comonomer into the TFE copolymer to make it melt fabricable, which amount will depend on the reactivity of the comonomer relative to TFE and the amount of incorporation necessary to impart melt-fabricability to the copolymer, this too depending on the particular comonomer used. Generally, the amount of comonomer incorporated into the TFE copolymer will be at least 0.5 mol % and may be as high as 15 mol % and even higher, depending on the comonomer. The goal of melt fabricability is demonstratable by the copolymer being processible by one or more melt-processing techniques such as extrusion, injection molding, compression molding and the like. Typically, the TFE copolymer will have a melt viscosity in the range of $10^2$ to $10^6$ Pa.s. Melt viscosity is determined by ASTM method D-1238, modified as disclosed in U.S. Pat. No. 4,360,618. The amount of copolymerizable comonomer used will usually be added to the reactor prior to the start of the polymerization reaction, but may also be added during the reaction if desired. One skilled in the art will recognize that a variety of comonomers can be used with TFE to achieve melt-fabricable TFE copolymer, and this variety can be used in the process of the present invention. Examples of copolymerizable perfluorinated monomers include perfluoroolefin such as HFP, or perfluoro(alkyl vinyl ether) (PAVE) wherein the alkyl group contains 1 to 8 carbon atoms, preferably 2 or 3 carbon atoms. More than one comonomer may be incorporated into the TFE copolymer, which, for example, may be a copolymer of TFE with HFP and PAVE.

Instead of the entire amount of the dispersing agent being added to the reactor at the beginning of the polymerization, a portion of the dispersing agent can be added during the polymerization reaction.

The preferred raw dispersion particle size (RDPS) of the TFE polymer particles is 50–350 nm. The amount of dispersing agent (I) of this invention used is effective to achieve the dispersion of polymer particles and preferably the preferred particle size within the range recited above.

The polymer particles produced by the dispersion polymerization process of this invention can be isolated from the aqueous raw dispersion by any convenient means, such as vigorous agitation, optionally supplemented by addition of electrolyte and/or water-immiscible solvent having low surface tension, or by freeze-thaw procedures, following by separation of polymer solids from the liquid and by drying. Alternatively, the raw dispersion can be stabilized, or concentrated and stabilized, for use in various applications such as metal coating, glass cloth coating, impregnation, and the like.

EXAMPLES

A shorthand notation is used to identify surfactants of this invention used in polymerization examples below. This notation is summarized in Table 1.

TABLE 1

Nomenclature Summary

| Nickname | Formula |
|---|---|
| H2—C9 | $C_6F_{13}$—$CH_2$—$CF_2$—$COONH_4$ |
| H4—C8 | $C_4F_9$—$CH_2CH_2$—$CF_2$—$COONH_4$ |
| H4—C8CF$_3$ | $C_4F_9$—$CH_2CH_2$—$CF(CF_3)$—$COONH_4$ |
| H6—C9K | $C_4F_9$—$CH_2CH_2CH_2$—$CF_2$—COOK |

The solids content of aqueous dispersions was determined gravimetrically.

The size of as-polymerized polymer particles (raw dispersion particle size, RDPS) was measured by photon correlation spectroscopy.

The standard specfic gravity (SSG) of coagulated and dried PTFE dispersion was measured according to ASTM D-4895. SSG is an indirect measure of molecular weight, with SSG decreasing with increasing molecular weight.

Example 1

Preparation of $ICF_2CF_2OSO_2F$

A 1-liter pressure reactor was charged a mixture of iodine monochloride (162.5 g, 1.0 mol) and flurosulfonic acid (110 g, 1.1 mol). The reactor was cooled and TFE (120 g, 1.2 mol) was added. After the addition of TFE was complete, the reaction mixture was heated at 100° C. for 10 hr. The cooled mixture was then slowly poured into a large amount of ice with stirring. The lower layer was separated, washed with diluted water, and dried over $MgSO_4$. Distillation isolated 2-iodo-1,1,2,2-tetrafluoroethyl fluorosulfate, formula above, as a clear liquid (215 g, 66% yield) having a boiling point of 87°–88° C.

Example 2

Preparation of $ICF_2CF_2OSO_2Cl$

A 1-liter pressure reactor was charged a mixture of iodine monochloride (390 g, 2.4 mol) and chlorosulfonic acid (490 g, 4.206 mol). The reactor was cooled and kept at 0°–10°C. until 300 g of TFE (3.0 mol) were added. After the addition of TFE was complete, the reaction mixture was hold at 0°–10° C. for 6 hr, then at 25° C. for 2 hr and then at 50°C. for 2 hr. The reaction mixture was then slowly poured into a large amount of ice with stirring, and worked up as described in Example 1. The procedure gave 610 g (74% yield) of 2-iodo-1,1,2,2-tetrafluoroethyl chlorosulfate, formula above, as a clear liquid having a boiling point of 62°–64° C. at 50 mmHg.

Example 3

Preparation of $ICF_2CO_2Et$ (a) From 2-Iodo-1,1,2,2-tetrafluoroethyl chlorosulfate:

A 500 mL flask was charged with sodium fluoride (18.9 g, 0.45 mol) and absolute ethanol (200 mL) and cooled in an ice-water bath. 2-Iodo-1,1,2,2-tetrafluoroethyl chlorosulfate (103 g, 0.3 mol) was added slowly. The reaction was exothermic and the reaction temperature was controlled at 20°–30° C. After addition, the reaction mixture was stirred at room temperature for 10 hr and then poured into cold water. The organic layer was separated, washed with saturated NaCl solution and dried over $MgSO_4$. Evaporation of the solvent in vacuo followed by distillation gave the ethyl iododifluoroacetate product (68.1 g, 91% yield, formula above) having a boiling point of 57°–58° C. at 30 mmHg. (b) From 2-iodo-1,1,2,2-tetrafluoroethyl fluorosulfate:

Ethyl iododifluoroacetate (53.4 g, 74% yield) was also prepared from 2-iodo-1,1,2,2-tetrafluoroethyl fluorosulfate (140.4 g, 0.4 mol), potassium fluoride (23.2 g, 0.4 mol), and ethanol (150 mL) according to the procedure described in (a).

Example 4

Preparation of $CF_3$—CFI—$CF_2OSO_2F$

A 1.3-liter stainless steel shaker tube was charged a mixture of iodine monochloride (130 g, 0.80 mol) and fluorosulfonic acid (88 g, 0.88 mol). The tube was sealed and cooled, then hexafluoropropylene (144 g, 0.96 mol) was transferred into the tube. The reaction mixture was kept at 25° C. for 2 hr, at 50° C. for 2 hr, and at 80° C. for 4 hr. The product unloaded from the shaker tube was poured into ice water, and the bottom organic layer was separted, washed with water, and distilled to give 120 g of 2-iodo-hexafluoropropyl fluorosulfate (formula above, 40% yield) as a clear liquid having a boiling point of 47° C. at 50 mmHg.

Example 5

Preparation of $C_4F_9$—$CHICH_2$—$CF_2$—$COOC_2H_5$

A 400 mL stainless steel shaker tube was charged perfluorobutyl ethylene ($C_4F_9$-CH=$CH_2$, 86.6 g, 0.352 mol), ethyl iododifluoroacetate (I-$CF_2$-$COOC_2H_5$, 87.5 g, 0.35 mol) and copper powder (dendritic, 3 micron, 2178 g, 0.044 mol). The tube was sealed and heated at 140° C. for 8 hr under agitation. After cooling, the tube was unloaded and the contents were filtered to remove any metal residue. The filtrate was distilled to obtain ethyl 4-iodo-2,2,5,5,6,6,7,7,8,8,8-undecafluorooctanoate, formula above, as a clear, pale pink liquid.

Example 6

Preparation of $C_4F_9$—$CH_2CH_2$—$CF_2$—$COOC_2H_5$

The compound ethyl 4-iodo-2,2,5,5,6,6,7,7,8,8,8-undecafluorooctanoate prepared from Example 5 (99.2 g, 0.2 mol) was added dropwise into a well-stirred tributyltin hydride liquid (58.5 g, 0.201 mol). The reaction temperature was controlled at ~30° C. during the process. After addition was complete, the mixture was stirred at 50° C. for 2 hr. The product ethyl 2,2,5,5,6,6,7,7,8,8,8-undecafluorooctanoate (65.0 g, 88% yield) was isolated by distillation as a clear, colorless liquid having a boiling point of 38°–39° C. at 3 mmHg.

Example 7

Preparation of $C_4F_9$—$CH_2CH_2$—$CF_2$—COONa

A mixture of ethyl 2,2,5,5,6,6,7,7,8,8,8-undecafluorooctanoate (46.4 g, 0.125 mol), sodium hydroxide (5.11 g, 0.128 mol), water (80 mL) and methanol (80 mL) was stirred at ambient temperature for 2 hr and at 50° C. for 2 hr. After cooling, ethyl acetate was added to extract the product. The organic layer was washed with brine and dried over magnesium sulfate, and then the solvent was removed in vacuo. After drying overnight under high vacuum, 44 g (96% yield) of sodium 2,2,5,5,6,6,7,7,8,8,8-undecafluorooctanoate was obtained as a white solid having a melting point of 155°–157° C.

Example 8

Preparation of $C_4F_9$—$CH_2CH_2$—$CF_2$—COOH

Ethyl 2,2,5,5,6,6,7,7:8,8,8-undecafluorooctanoate (3 g, 8.1 mol) was mixed with 20% aqueous sodium hydroxide solution (20 mL) and stirred at 50° C. for 30 min. At this time, the solution turned into a gel-like mixture. 6N aqueous HCl was added slowly with stirring to adjust the pH of the solution to about 1.0, and then ether was added to extract the product. The organic layer was washed with water, and dried under high vacuum to give 2.4 g (86.5% yield) of product 2,2,5,5,6,6,7,7,8,8,8-undecafluorooctanoic acid as a white solid having a melting point of 47° C.

Example 9

Preparation of $C_4F_9$—$CH_2CH_2$—$CF_2$—$COONH_4$ (H4—C8)

2,2,5,5,6,6,7,7,8,8,8-undecafluorooctanoic acid (30 g, 0.0877 mol) was dissolved in ether (100 mL) and cooled to 15° C. Concentrated ammonium hydroxide (28 wt %, aqueous, 6.1 mL, 0.09 mol) was added slowly into the solution while the reaction mixture was warmed to ambient temperature and the solvent was removed in vacuo. The residue was dried overnight under high vacuum to give the product ammonium 2,2,5,5,6,6,7,7,8,8,8-undecafluorooctannoate, formula above, as a white solid fine powder having a melting point of 151°–152° C. The yield was almost quantitative.

Example 10

Preparation of $CF_3$—CFI—$COOC_2H_5$

A 500 mL flask was charged with potassium fluoride (17.5 g, 0.31 mol) and absolute ethanol (110 mL), and was cooled in an ice-water bath. 2-iodo-hexafluoropropyl fluorosulfate (112.8 g, 0.3 mol) was added slowly. The reaction was exothermic and the reaction temperature was controlled at 20°–25° C. After addition was complete, the reaction mixture was heated at 70° C. for 4 hr and then poured into cold water. The bottom organic layer was separated, washed with saturated NaCl aqueous solution and dried over $MgSO_4$. Evaporation of the solvent in vacuo followed by distillation gave 50 g (56% yield) of ethyl 2-iodotetrafluoropropionate product, formula above, having a boiling point of 60°–65° C. at 50 mmHg.

Example 11

Preparation of $C_4F_9$—$CHICH_2$—$CF(CF_3)$—$COOC_2H_5$

A 400 mL stainless steel shaker tube was charged with perfluorobutyl ethylene ($C_4F_9$—CH=$CH_2$, 70 g, 0.284 mol), 2-iodo-hexafluoropropyl fluorosulfate ($CF_3$—CFI—$CF_2OSO_2F$, 84 g, 0.28 mol) and copper powder (dendritic, 3 micron, 1.90 g, 0.03 mol). The tube was sealed and heated at 155° C. for 6 hr under agitation. After cooling, the tube was unloaded and and the contents were filtered to remove any metal residue. The filtrate was distilled to obtain 97 g (63.4% yield) of ethyl 4-iodo-2-trifluoromethyl-2,5,5,6,6,7,7,8,8,8-decafluorooctanoate product, formula above, as a clear, pale pink liquid having a boiling point of 62°–65° C. at 2 mmHg. This product was a mixture of diastereomers.

Example 12

Preparation of $C_4F_9$—$CH_2CH_2$—$CF(CF_3)$—$COOC_2H_5$

Ethyl 4-iodo-2-trifluoromethyl-2,5,5,6,6,7,7,8,8,8-decafluorooctanoate prepared as in Example 11 (25.7 g, 0.047 mol) was added dropwise into a well-stirred tributyltin hydride liquid (13.7 g, 0.047 mol). The reaction temperature was controlled at ~30° C. during the process. After addition was complete, the mixture was stirred at 50° C. for 2 hr. Distillation isolated 16.4 g (83% yield) of product ethyl 2-trifluoromethyl-2,5,5,6,6,7,7,8,8,8-decafluorooctanoate, formula above, as a clear, colorless liquid having a boiling point of 42°–45° C. at 4 mmHg.

Example 13

Preparation of $C_4F_9$—$CH_2CH_2$—$CF(CF_3)$—COONa

A mixture of ethyl 2-trifluoromethyl-2,5,5,6,6,7,7,8,8,8-decafluoro-octanoate (14.8 g, 0.035 mol), sodium hydroxide (1.64 g, 0.041 mol), water (25 mL) and methanol (25 mL) was stirred at ambient temperature for 2 hr and at 60° C. for 2 hr. After cooling, ethyl acetate was added to extract the product. The organic layer was separated, washed with brine, and dried over magnesium sulfate, and then the solvent was removed in vacuo. After drying overnight under high vacuum, the sodium 2-trifluoromethyl-2,5,5,6,6,7,7,8,8,8-decafluorooctanoate salt product, formula above, was obtained as a white to light brown low melting point solid in almost quantitative yield.

Example 14

Preparation of $C_4F_9$—$CH_2CH_2$—$CF(CF_3)$—COOH

Sodium 2-trifluoromethyl-2,5,5,6,6,7,7,8,8,8-decafluorooctanoate was dissolved in water with vigorous stirring and 6N aqueous hydrochloric acid was added slowly to adjust the pH of the solution to about 1.0, and then ether was added to extract the product. The organic layer was separated, washed with water, and dried over magnesium sulfate. After removal of the solvent in vacuo, the residue was dried under high vacuum to give quantitative yield of 2-trifluoromethyl-2,5,5,6,6,7,7,8,8,8-decafluorooctanoic acid, formula above, as a white solid having a melting point of 45°–46° C.

Example 15

Preparation of $C_4F_9$—$CH_2CH_2$—$CF(CF_3)$—$COONH_4$ ($H_4$—$C8CF_3$)

2-trifluoromethyl-2,2,5,5,6,6,7,7,8,8,8-undecafluorooctanoic acid (11 g, 0.028 mol) was dissolved in anhydrous ether (30 mL) and cooled to 15° C. Concentrated ammonium hydroxide (28 wt. %, aqueous, 2.0 mL, 0.029 mol) was added slowly into the ether solution while the reaction temperature was controlled at ≦20° C. After addition was complete, the reaction mixture was warmed to ambient temperature and the solvent was removed in vacuo. The residue was dried overnight under high vacuum to give 10.4 g (91 % yield) of the product ammonium 2-trifluoromethyl-2,5,5,6,6,7,7,8,8,8-decafluorooctanoate as a white solid fine powder having a melting point of 191°–192° C.

Example 16

Preparation of $C_6F_{13}$—$CHICH_2$—$CF_2$—$COOC_2H_5$

A 400 mL stainless steel shaker tube was charged perfluorohexyl-ethylene ($C_6F_{13}$—CH=$CH_2$, 103.8 g, 0.3 mol), ethyl iododifluoroacetate (75 g, 0.3 mol) and copper powder (dendritic, 3 micron, 2.4 g, 0.0378 mol). The tube was sealed and heated at 170° C. for 8 hr under agitation. After cooling, the tube was unloaded and the contents were filtered to remove any metal residue. The filtrate was distilled to obtain 115 g (64.3 % yield) of the product ethyl 4-iodo-2,2,5,5,6,6,7,7,8,8,9,9,10,10,10 pentadecafluorodecanoate as a clear, pale pink liquid having a boiling point of 80° C. at 0.3 mmHg.

Example 17

Preparation of $C_6F_{13}$—$CH_2CH_2$—$CF_2$—$COOC_2H_5$

The compound ethyl 4-iodo-2,2,5,5,6,6,7,7,8,8,9,9,10,10,10-pentadecafluoro-decanoate from Example 16 (107.3 g, 0.18 mol) was added dropwise into a well-stirred tributyltin hydride liquid (53 g, 0.182 mol). The reaction temperature was controlled at ~30° C. during the process. After addition was complete, the mixture was stirred at 50° C. for 2 hr. Distillation isolated 78.0 g (92% yield) of product ethyl 2,2,5,5,6,6,7,7,8,8,9,9,10,10,10-pentadecafluorodecanoate as a clear, colorless liquid having a boiling point of 53° C. at 1.0 mmHg.

Example 18

Preparation of $C_6F_{13}$—$CH_2CH_2$—$CF_2$—COOH

Ethyl 2,2,5,5,6,6,7,7,8,8,9,9,10,10,10-pentadecafluorodecanoate (72 g, 0.153 mol) was mixed with 20% aqueous sodium hydroxide solution (250 mL) and stirred at 50° C. for 1 hr. At this time, the solution was a gel-like mixture. 6N aqueous HCl was added slowly with stirring to adjust the pH of the solution to about 1.0, and then ether was added to extract the product. The organic layer was separated, washed with water, dried over magnesium sulfate. After removal of the solvent in vacuo, the residue was dried under high vacuum to obtain 65.5 g (96.7 % yield) of the product 2,2,5,5,6,6,7,7,8,8,9,9,10,10,10-pentadecafluorodecanoic acid as a white solid having a melting point of 53°–54° C.

Example 19

Preparation of $C_6F_{13}$—$CH_2CH_2$—$CF_2$—$COONH_4$ 2,2,5,5,6,6,7,7,8,8,9,9,10,10,10-pentadecafluorodecanoic acid (63.5 g, 0.1437 mol) was dissolved in ether (175 mL) and the solution was cooled to 15° C. Concentrated ammonium hydroxide (28 wt %, aqueous, 10 mL, 0.15 mol) was added slowly into the ether solution while the reaction temperature was controlled at ≦20° C. After addition was complete, the reaction mixture was warmed to ambient temperature and the solvent was removed in vacuo. The residue was dried overnight under high vacuum to give 58.6 g (89% yield) of the product ammonium 2,2,5,5,6,6,7,7,8,8,9,9,10,10,10-pentadecafluorodecanoate as a white solid fine powder having a melting point of 158° C.

Example 20

Preparation of $C_4F_9$—$CH_2CH$=$CH_2$

A mixture of perfluorobutyl iodide (103.8 g, 0.3 mol), copper powder (50 g, 0.79 mol) and dimethyl sulfoxide (150 mL) was stirred at 110°–120° C. for 2 hr, then cooled to room temperature. Allyl bromide (36.3 g, 0.3 mol) was added dropwise and then the mixture was stirred at room temperature for 2 hr and at 50° C. for 1 hr. The reaction mixture was distilled in vacuo and the crude product was collected in a cold trap (−78° C.). Redistillation produced 55.2 g (70% yield) of the desired 4,4,5,5,6,6,7,7,7-nonafluoro-1-heptene, formula above, having a boiling point of 79°–80° C.

Example 21

Preparation of $C_4F_9$—$CH_2$—$CHICH_2$—$CF_2$—$COOC_2H_5$

A mixture of ethyl iododifluoroacetate (130 g, 0.52 mol), 4,4,5,5,6,6,7,7,7-nonafluoro-1-heptene (130 g, 0.5 mol) and copper powder (3.2 g, 0.05 mol) was heated at 70° C. for 4 hr with stirring. After cooling to room temperature, the reaction mixture was filtered to remove any metal residue. The filtrate was distilled under reduced pressure to produce 225 g (88% yield) of ethyl 4-iodo-2,2,6,6,7,7,8,8,9,9,9-undecafluorononanoate, formula above, as a clear colorless liquid having a boiling point of 83°–85° C. at 0.3 mmHg.

Example 22

Preparation of $C_4F_9$—$CH_2CH_2CH_2$—$CF_2$—$COOC_2H_5$

Ethyl 2,2,6,6,7,7,8,8,9,9,9-undecafluorononanoate (17.3 g, 90% yield) was prepared from ethyl 4-iodo-2,2,6,6,7,7,8,8,9,9,9-undecafluorononanoate (25.5 g, 50 mmol), tributyltin hydride (16.0 g, 55 mmol) and anhydrous ether (100 mL) according to the procedure of Example 6. Boiling point was 53°–55° C. at 0.7 mmHg.

Example 23

Preparation of $C_4F_9$—$CH_2CH_2CH_2$—$CF_2$—COONa

Sodium 2,2,6,6,7,7,8,8,9,9,9-undecafluoro-nonanoate (60 g, 99% yield, formula above) was prepared from ethyl 2,2,6,6,7,7,8,8,9,9,9-undecafluorononanoate (61.5 g, 0.16 mol), sodium hydroxide (6.5 g, 0.163 mol), water (100 mL) and methanol (100 mL) according to the procedure of Example 7.

Example 24

Preparation of $C_4F_9$—$CH_2CH_2CH_2$—$CF_2$—COOK

Potassium 2,2,6,6,7,7,8,8,9,9,9-undecafluorononanoate (69.2 g, 98% yield, formula above, H6-C9K) was prepared from ethyl 2,2,6,6,7,7,8,8,9,9,9-undecafluorononanoate (69.1 g, 0.18 mol), potassium hydroxide (10.5 g, 0.188 mol), water (150 mL) and methanol (150 mL) according to the procedure of Example 7.

Example 25

TFE Polymerization Using H6—C9K

A 400 mL stainless shaker tube was charged with deionized water (250 mL), potassium 2,2,6,6,7,7,8,8,9,9,9-undecafluorononanoate (2 g, Example 24) and ammonium persulfate (APS, 0.4 g in 5 mL of water). The tube was sealed, cooled and evacuated, and then TFE (45 g) was transferred into the tube. The tube was heated at 70° C. for 4 hr under agitation. After the workup and drying (150 mmHg, 100° C. for 24 hr), 43.5 g of white 15 polymer were obtained. This polymer exhibited a $T_m$ at 332.2° C. (second heat curve) as measured by DSC (Differential Scanning Calorimetry).

Example 26

TFE/PMVE Polymerization Using H4—C8

A 400 mL stainless steel shaker tube was charged deionized water (260 mL), ammonium 2,2,5,5,6,6,7,7,8,8,8-undecafluorooctanoate (H4—C8, 1.5 g), disodium hydrogen phosphate (0.5 g) and APS (0.2 g). The tube was sealed, then TFE (45 g) and perfluoro(methyl vinyl ether) (PMVE, 36 g) were transferred into the tube. The tube was heated at 70° C. for 4 hr under agitation. The polymer emulsion unloaded from the shaker tube was coagulated with dilute nitric acid, and the polymer precipitated was collected by filtration and washed with warm water (70° C.) several times. After drying in vacuum oven (100 mmHg) at 100° C. for 24 hr, 70 g of white polymer were obtained. This polymer exhibited a glass transition temperature at −200 C. by DSC measurement. No crystalline melting point was observed.

Example 27

TFE Polymerization Using H4—C8

A 400 mL stainless shaker tube was charged distilled water (280 mL), H4—C8 (1.5 g), and APS (0.4 g in 5 mL of water). The tube was sealed, cooled and evacuated, and then TFE (45 g) was transferred into the tube. The tube was heated at 70° C. for 4 hr under 35 agitation. After working up and drying (150 mmHg, 100° C. for 24 hr), 42.5 g of white polymer solids were obtained. This polymer has exhibited a $T_m$ at 332.4° C. (second heat curve) as measured by DSC.

Example 28

TFE/HFP Copolymenzation Using H4—$C8CF_3$

A 4-L horizontal autoclave with mechanical agitator was purged with nitrogen and charged with 2 L of distilled water and 4.25 g of $C_4F_9$—$CH_2CH_2CF(CF_3)CO_2NH_4$ (H4—$C8CF_3$). The reactor was closed, the contents were heated to 103° C. and agitated at 90 rpm. The reactor was flushed with a mixture of 70 wt % hexafluoropropylene (HFP) and 30 wt % TFE, and was then pressured to 4.5 MPa with this gas mixture. A solution prepared by dissolving 4 g of APS in 1 L of distilled water was injected at the rate of 6 mL/min for 12 min. Then a solution prepared by dissolving 7 g of potassium persulfate (KPS) in 1 L of distilled water was injected at the rate of 1 mL/min and pressure in the reactor was maintained at 4.5 MPa by addition of TFE. A total of 840 g of TFE was added over 101 min.

The initiator and TFE flows were halted, the reactor was allowed to cool and was vented to atmospheric pressure. The reactor contents were discharged as a latex with about 2 inches of coagulum on the surface. This mixture was frozen in dry ice, thawed, and filtered. The solid polymer was stirred with about 2 L of distilled water at 80° C., filtered, and dried in a vacuum oven at about 120° C. overnight under a flow of nitrogen. The amount of polymer isolated was 974.9 g as a fluffy white powder. By $^{19}F$ NMR analysis of the melt at 320° C., the polymer was determined to contain 9.98 wt % of HFP. The polymer extruded at 0.532 g/min in a melt index apparatus at 372° C. with a 15 kg weight.

Example 29

TFE/HFP Copolymerization Using H4—C8

The procedure of Example 28 was essentially followed, except that 3.73 g of $C_4F_9CH_2CH_2CF_2CO_2NH_4$ surfactant (H4—C8) were used in place of H4—$C8CF_3$, and the time for addition of 840 g of TFE was 126 min. The amount of polymer isolated as a fluffy white powder was 966.3 g. By $^{19}F$ NMR analysis of the melt at 320° C., the polymer was determined to contain 10.13 wt % of HFP. The polymer had a melting point of 269.3° C. with heat of fusion of 20.4 J/g, and extruded at 1.19 g/min in a melt index apparatus at 372° C. with a 15 kg weight.

Example 30

TFE/HFP Copolymerization Using H4—C8

The procedure of Example 29 was essentially followed, except that 4.8 g of H4—C8 were used. A total of 846.2 g of TFE was added over 105 min. The reactor contents were discharged as a latex with less than 1 inch of coagulum on the surface, and 1020.4 g of polymer were isolated as a fluffy white powder. The polymer contained 10.65 wt % of HFP, had a melting point of 264.3° C. with 18.0 J/g heat of fusion, and extruded at 0.55 g/min in a melt index apparatus at 372° C. with a 15 kg weight.

Example 31 and Control A

TFE Polymerization Using H4—C8

A horizontally disposed, cylindrical, stainless steel autoclave, having a nominal capacity of 1 gal (3.8 L) and provided with a four-bladed agitator was charged with 1800 mL of demineralized water, 40 g of paraffm wax, and a chosen amount of surfactant as shown in Table 2. The reactor was pressure tested at 400 psig (2.86 MPa) and 75° C. while stirring at 100 rpm. Then the reactor was cooled to 65° C., and was evacuated and purged with TFE three times. After bringing the reactor to operating conditions of 80° C. and 110 rpm, it was pressurized with TFE to 400 psig and, except as otherwise indicated, a freshly prepared aqueous solution of 0.8 g of disuccinic peroxide (DSP) in 100 mL of demineralized water was pumped into the reactor at a rate of 50 mL/min. to initiate polymerization. After polymerization began, as indicated by a 10 psi (0.04 MPa) pressure drop, additional TFE was added to maintain a constant pressure of 400 psig. After 1180 g of TFE had been added to the reactor, including the initial charge, the TFE feed was stoped but the reaction was continued until the reactor pressure decreased to 250 psig (1.82 MPa). The reactor was then vented, cooled to room temperature, and the PTFE raw dispersion was discharged. Solids content and raw dispersion particle size (RDPS) are listed in Table 2. A portion of the dispersion was diluted to 15 wt % solids with demineralized water and was coagulated with vigorous stirring, and the resultant powder was collected on a filter and dried at 150° C. The standard specific gravity (SSG) of this powder is also given in Table 2. The low SSG values for the PTFE made using H4—C8 reflect high molecular weight and indicate a very low level of chain transfer activity for the surfactant of this invention. Note that doubling of the initiator amount yielded an SSG comparable to that obtained when using C-8 in the Controls.

TABLE 2

Surfactant Concentration and Results for Ex. 31 and Control A

| Ex. | Surfactant Type | Conc.(g/L) | Solids (wt %) | RDPS (nm) | SSG |
|---|---|---|---|---|---|
| A-1 | C-8 | 1.6 | 33.0 | 218 | 2.1909 |
| A-2 | C-8 | 2.4 | 35.3 | 229 | 2.1955 |
| 31-1 | H4—C8 | 0.8 | 28.9 | 271 | 2.1865 |
| 31-2 | H4—C8 | 1.6 | 34.9 | 249 | 2.1772 |
| 31-3 | H4—C8 | 3.2 | 31.1 | 237 | 2.1761 |
| 31-4 | H4—C8 | 4.8 | 32.9 | 239 | 2.1775 |

Example 32 and Control B

TFE Polymerization Using H6—C9K

The same experimental procedure described above for the H4—C8 surfactant was essentially followed, but using $F_9C_4$—$CH_2CH_2CH_2$—$CF_2COOK$ (H6—C9K) as the surfactant. The results of these polymerizations are presented in Table 3. As in Example 31, the SSG values obtained when using H6—C9K indicate a low level of chain transfer activity for the surfactant of this invention.

TABLE 3

Surfactant Concentration and Results for Ex. 32 and Control B

| Ex. | Surfactant Type | Conc.(g/L) | Solids (wt %) | RDPS (nm) | SSG |
|---|---|---|---|---|---|
| B-1 | C-8 | 1.6 | 39.9 | 241 | 2.210 |
| B-2 | C-8 | 1.6 | 31.3 | 234 | 2.202 |
| 32-1 | H6—C9K | 0.6 | 31.1 | 210 | 2.199 |
| 32-2 | H6—C9K | 1.2 | 29.4 | 208 | 2.196 |

Example 33 and Control C

TFE Polymerization Using 4H—$C8CF_3$

The same experimental procedure described above for the H4—C8 surfactant was essentially followed, but using $F_9C_4$—$CH_2CH_2$—$CF(CF_3)$—$COONH_4$ (H4—C8CF3) as the surfactant. The results of these polymerizations are presented in Table 4. As in the preceding Examples, the low SSG values obtained when using H4—$C8CF_3$ reflect high molecular weight and indicate a low level of chain transfer activity for the surfactant of this invention.

TABLE 4

Surfactant Concentration and Results for Ex. 33 and Control C

| Ex. | Surfactant Type | Conc.(g/L) | Solids (wt %) | RDPS (nm) | SSG |
|---|---|---|---|---|---|
| 32-1 | C-8 | 1.6 | 33.4 | 258 | 2.1849 |
| 32-2 | C-8 | 1.1 | 34.6 | 252 | 2.1892 |
| C-1 | H4—C8CF3 | 0.8 | 32.0 | 249 | 2.1865 |
| C-2 | H4—C8CF3 | 1.6 | 30.5 | 261 | 2.1812 |

Example 34

Synthesis of $C_6F_{13}$—$CH_2$—$CF_2$—$COONH_4$

H2—C9, formula above, was prepared in a series of steps, as follows.

(i) Preparation of $C_6F_{13}$ $_{—CH2}$$CF_2CH_2CF_2I$

A 1-L autoclave was charged with 223 g of $C_6F_{13}I$. After being cooled to −78° C., the autoclave was evacuated and 40 g of $CF_2$=$CH_2$ were added. The mixture was heated at 210° C. for 15 hr and then distilled to separate residual $C_6F_{13}I$ and various adducts of $C_6F_{13}I$ and $CF_2$=$CH_2$, including 55.0 g of 1:2 adduct having a boiling point of 87°–88° C. at 10 mmHg. GC analysis of the 1:2 adduct indicated it to be a 92:8 mixture of $C_6F_{13}$—$CH_2$—$CF_2$—$CH_2$—$CF_2I$ and $C_6F_{13}$—$CH_2$—$CF_2$—$CF_2$—$CH_2I$, respectively. The structures were confirmed by $^{19}F$ and proton NMR.

(ii) Preparation of $C_6F_{13}$—$CH_2$—$CF_2$—$CH_2$=$CF_2$

A mixture of 100 g of $C_6F_{13}$—$CH_2$—$CF_2$—$CH_2$—$CF_2I$ and 11.0 g of LiCl in 90 mL of dimethyl formamide was slowly heated to 150° C. at 150–200 mmHg for 3.5 hr, during which volatiles were distilled out and collected in a −10° C. receiver. A lower layer was separated, washed with brine and distilled to give 61.2 g of $C_6F_{13}$—$CH_2$—$CF_2$—$CH_2$=$CF_2$ (identified by $^{19}F$ and proton NMR and by elemental analysis) having a boiling point of 92°–94° C. at 100 mmHg.

(iii) Preparation of $C_6F_{13}$—$CH_2$—$CF_2$—COOH

A mixture of 12.6 g of $KMnO_4$, 55 g of water, 7.3 g of concentrated $H_2SO_4$ and 11.2 g of $C_6F_{13}$—$CH_2$—$CF_2$—$CH_2$=$CF_2$ was heated at 80°–90° C. for 5 hr. After being cooled to room temperature, the mixture was treated with $Na_2SO_3$ to remove $MnO_2$. 50 mL of 10% $H_2SO_4$ were added, and then the mixture was extracted with ether. The ether layer was washed with 5% $H_2SO_4$ and dried over $Na_2SO_4$. After removal of the ether, 9.8 g of solid were recrystalized from hexane to yield 8.4 g of $C_6F_{13}$—$CH_2$—$CF_2$—COOH (confirmed by $^{19}F$ NMR).

(iv) Preparation of $C_6F_{13}$—$CH_2$—$CF_2$—$COONH_4$ $C_6F_{13}$—$CH_2$—$CF_2$—COOH (7.0 g) was dissolved in 25 mL of ether. While stirring the solution at room temperature, excess $NH_3$ was added through a dry-ice condenser. After removal of valotiles, 6.8 g of $C_6F_{13}$—$CH_2$—$CF_2$—$COONH_4$ (H2—C9) were obtained as a white solid ($^{19}F$ and proton NMR).

Example 35

Synthesis of $C_6F_{13}$—$CH_2$—$CF_2$—$CO_2NH_4$

H2—C9, formula above, was prepared in a series of steps, as follows.

(i) Preparation of $C_6F_{13}$—CH=$CF_2$

A mixture of 107g of $C_6F_{13}$—$CH_2$—$CF_2I$ (the 1:1 adduct of $C_6F_{13}I$ and $CF_2$=$CH_2$, obtained as described in Example 34) and 14.0 g of LiCl in 115 mL of DMF was slowly heated to 150° C. for 3.5 hr while volatiles were distilled out and collected in a receiver cooled to −10° C. A lower layer in the distillate was separated and washed with brine and water to give 77.8 g of crude product, which was distilled to give 66.4 g of $C_6F_{13}$—CH=$CF_2$ (confirmed by $^{19}F$ NMR) having a boiling point 110°–111° C.

(ii) Preparation of $C_6F_{13}$—$CH_2$—$CF_2$—$CH_2OH$

A mixture of 30 g of $C_6F_{13}$—$CH_2$=$CF_2$, 14.0 g of MeOH and 1.6 g of di-tert-butyl peroxide was heated in a sealed tube at 145° C. for 14 hr. After removal of volatiles, 31.8 of $C_6F_{13}$—$CH_2$—$CF_2$—$CH_2OH$ was obtained. The structure was confirmed by $^{19}F$ and proton NMR and by infrared spectroscopy.

(iii) Preparation of $C_6F_{13}$—$CH_2$—$CF_2$—COOH $C_6F_{13}$—$CH_2$—$CF_2$—$CH_2OH$ (30 g) in 100 mL of acetone and 50 mL of ether were added to a large excess of Jones' reagent (prepared from 110 g of $CrO_3$, 55 mL of concentrated sulfuric acid and 550 mL of water) and maintained overnight at room temperature to 40° C. The reaction mixture was extracted with ether, and the ether layer was washed with water and dried over $Na_2SO_4$. After removal of the ether, 22.9 g of white solids were obtained, which were recrystallized from hexane to give 18.2 g of $C_6F_{13}$—$CH_2$—$CF_2$—COOH. The acid was converted to the ammonium salt as described in example 34.

Example 36

TFE/HFP Copolymerization Using H2—C9

The procedure of Example 28 was essentially followed, except that 4.6 g of $C_6F_{13}CH_2CF_2COONH_4$ surfactant (H2—C9) were used in place of H4—C8$CF_3$. A total of 841 g of TFE was added over 94 min. The reactor contents were discharged as a latex with less than 1 inch of coagulum on the surface, and 963.1 g of polymer were isolated as a fluffy white powder. The polymer contained 10.04 wt % of HFP, had a melting point of 264.4° C. with 15.0 J/g heat of fusion, and extruded at 0.26 g/min in a melt index apparatus at 372° C. with a 15 kg weight.

What is claimed is:

1. A compound having the formula $R_f$—$(CH_2)_m$—$R'_f$—COOY, wherein m is 1–3, $R_f$ is perfluoroalkyl or perfluoroalkoxy containing 3–8 carbon atoms, $R'_f$ is linear or branched perfluoroalkylene containing 1–4 carbon atoms, Y is M or R, M is $NH_4$, Li, Na, K or H, and R is linear, branched or cyclic alkyl containing 1–8 carbon atoms.

2. The compound of claim 1, wherein $R_f$ is perfluoroalkyl.

3. The compound of claim 1, wherein m is 1 or 2, $R_f$ is linear perfluoroalkyl having 4–6 carbon atoms, $R'_f$ is linear perfluoroalkylene having 1–2 carbon atoms, Y is M, and M is $NH_4$ or H.

4. The compound of claim 1, wherein m is 1 or 2, $R_f$ is linear perfluoroalkyl having 4–6 carbon atoms, $R'_f$ is linear perfluoroalkylene having 1–2 carbon atoms, Y is R, and R is methyl or ethyl.

5. A compound having the formula $R_f(CH_2)_x$—CHI—$(CH_2)_y$—$R'_f$—COOR, wherein x and y are independently 0 or 1, $R_f$ is perfluoroalkyl or perfluoroalkoxy containing 3–8 carbon atoms, $R'_f$ is linear or branched perfluoroalkylene containing 1–4 carbon atoms, and R is linear, branched or cyclic alkyl containing 1–8 carbon atoms.

6. The compound of claim 5, wherein $R_f$ is linear perfluoroalkyl having 4–6 carbon atoms, $R'_f$ is linear perfluoroalkylene having 1–2 carbon atoms, and R is methyl or ethyl.

7. A compound having the formula $R_f$—$CH_2$—$R'_f$—A, wherein $R_f$ is perfluoroalkyl or perfluoroalkoxy containing 3–8 carbon atoms, $R'_f$ is linear or branched perfluoroalkylene containing 1–4 carbon atoms, and A is $CF_2I$ or $CH_2OH$.

8. The compound of claim 7, wherein $R_f$ is linear perfluoroalkyl having 4–6 carbon atoms, $R'_f$ is linear perfluoroalkylene having 1–2 carbon atoms.

9. A process comprising polymerizing at least one fluorinated monomer in an aqueous medium containing initiator and dispersing agent to obtain an aqueous dispersion of particles of fluoropolymer, wherein said dispersing agent is a compound having the formula $R_f$—$(CH_2)_m$—$R'_f$—COOM, wherein m is 1–3, $R_f$ is perfluoroalkyl or perfluoroalkoxy containing 3–8 carbon atoms, $R'_f$ is linear or branched perfluoroalkylene containing 1–4 carbon atoms, and M is $NH_4$, Li, Na, K, or H.

10. The process of claim 9, wherein said monomer is tetrafluoroethylene.

11. The process of claim 9, wherein said monomer is tetrafluoroethylene and at least one additional monomer.

12. The process of claim 9, wherein $R_f$ is perfluoroalkyl.

13. The process of claim 12, wherein wherein m is 1 or 2, $R_f$ is linear perfluoroalkyl having 4–6 carbon atoms, $R'_f$ is linear perfluoroalkylene having 1–2 carbon atoms, and M is $NH_4$.

* * * * *